(12) United States Patent
Lasater

(10) Patent No.: US 7,563,279 B2
(45) Date of Patent: Jul. 21, 2009

(54) STENT HAVING AN ULTRASONIC EMITTER

(75) Inventor: Brian J. Lasater, Wenatchee, WA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 739 days.

(21) Appl. No.: 11/157,646

(22) Filed: Jun. 20, 2005

(65) Prior Publication Data

US 2006/0287597 A1 Dec. 21, 2006

(51) Int. Cl.
*A61F 2/06* (2006.01)

(52) U.S. Cl. ........................ 623/1.43; 604/22

(58) Field of Classification Search ............... None
See application file for complete search history.

(56) References Cited

U.S. PATENT DOCUMENTS

| | | | |
|---|---|---|---|
| 5,193,539 A | 3/1993 | Schulman et al. |
| 5,193,540 A | 3/1993 | Schulman et al. |
| 5,324,316 A | 6/1994 | Schulman et al. |
| 6,051,017 A | 4/2000 | Loeb et al. |
| 6,164,284 A | 12/2000 | Schulman et al. |
| 6,185,455 B1 | 2/2001 | Loeb et al. |
| 6,656,162 B2 | 12/2003 | Santini, Jr. et al. |
| 6,723,064 B2 | 4/2004 | Babaev |
| 6,733,451 B2 | 5/2004 | Rabiner et al. |
| 6,764,519 B2 | 7/2004 | Whitmore, III |
| 6,849,069 B1 | 2/2005 | Clayman et al. |
| 2002/0002371 A1 * | 1/2002 | Acker et al. ............... 606/27 |
| 2002/0123787 A1 | 9/2002 | Weiss |
| 2003/0078634 A1 | 4/2003 | Schulman et al. |
| 2004/0158317 A1 | 8/2004 | Brisken et al. |
| 2004/0193177 A1 | 9/2004 | Houghton et al. |
| 2004/0220660 A1 | 11/2004 | Shanley et al. |
| 2004/0225350 A1 | 11/2004 | Shanley |

OTHER PUBLICATIONS

Associated Press, Ultrasonic Waves May Assist Drugs in Stroke Patients, Nov. 18, 2004, p. B8, Publisher: The Wall Street Journal.

* cited by examiner

*Primary Examiner*—Thomas J Sweet
*Assistant Examiner*—Jonathan R Stroud
(74) *Attorney, Agent, or Firm*—Gary D. Schnittgrund

(57) ABSTRACT

A system and method that minimizes plaque accumulation on a stent and thereby restenosis that could require a subsequent invasive medical procedure following stent implantation. The stent, essentially an expandable wire mesh tube comprised of a plurality of integral lattice portions, configured for expansion within a blood vessel of a patient, is formed with an electrically-controlled, biocompatible device as one of its integral lattice portions. In a first implementation, the biocompatible device is under control of an externally-positioned controller which causes the device to emit an ultrasonic wave at a frequency corresponding to the mechanical resonance of the stent and thereby minimize accumulation of plaque. In a second or supplemental implementation, the device is or other portions of the stent are coated with a drug that can be controllably eluted by passing a current through the coating under control of the biocompatible device and the externally-positioned controller.

3 Claims, 12 Drawing Sheets

OPEN LOOP CONTROL/MONITOR

CLOSED LOOP CONTROL

EXEMPLARY INJURY

COORDINATED CLOSED LOOP HAND CONTROL

STENT HAVING AN ULTRASONIC EMITTER

FIELD OF THE INVENTION

The present invention is generally directed to systems and methods for preventing restenosis following a stent procedure by using an electrically-powered, biocompatible device formed as an integral portion of the stent where the electrically-powered biocompatible device is under control of an externally-positioned control device that issues commands to the integral biocompatible device to use an electrically controlled signal to minimize plaque accumulation on the stent.

BACKGROUND OF THE INVENTION

Blockage of one or more of the arteries providing blood flow to the heart muscle of a patient can cause serious problems, ranging from symptomatic problems, e.g., chest pain, to heart attacks, and potentially death. In the most serious cases, the blocked arteries are bypassed using coronary artery bypass graft surgery (CABG) to enhance the blood flow to the sections of the heart at risk due to the restricted blood flow. While this is a relatively common procedure, it is still a serious invasive surgery that should be avoided if possible. Angioplasty, while still being an invasive procedure, is much less dangerous than bypass surgery and has much shorter recovery times. In angioplasty, a catheter is inserted, typically through the groin, into the blocked or partially blocked artery and a balloon at the distal end of the catheter is inflated to open up the blocked artery and renew blood flow to the heart portions at risk. Reclosure (restenosis) may occur, necessitating a repeat procedure. Alternatively or subsequently, a stent may be used instead or along with angioplasty. A stent is a wire mesh tube that is used to prop open a blocked artery. The stent is initially collapsed around a balloon catheter that is moved into the blocked artery. By inflating the balloon, the stent expands into a locked position and permanently forms a scaffold at the arterial position that previously experienced the blockage. This improves blood flow to the patient's heart and can relieve the symptoms, e.g., chest pain. It is reported that 70-90 percent of such procedures currently use stents. Unfortunately, restenosis may also be a problem with stents. To help to avoid such problems, prescription blood-thinning agents following surgery, e.g., ticlopidine or clopidogrel, are commonly used to avoid complications and aspirin is used indefinitely. To further help to avoid such problems, some stents, i.e., drug-eluting stents, include coatings which slowly release a drug, e.g., paclitaxel, sirolimus (also known as rapamycin) to prevent the blood vessel from reclosing. Such drug-eluting stents are known from Boston Scientific, e.g., their TAXUS Express stent, Cordis, e.g., their Cypher Sirolimus-Eluting Coronary Stent (Cypher stent), and the like. While such technologies are reported to be helpful, it is not believed that the problem of restenosis has been fully addressed. Furthermore, there are a finite number of times that a scaffolding procedure may be performed, leaving the patient with little or no remaining options.

SUMMARY OF THE INVENTION

The present invention is generally directed to systems and methods for preventing restenosis following a stent procedure by using an electrically-controlled biocompatible device under control of an externally-positioned control device that issues commands to the implanted device to use an electrically controlled signal to minimize plaque accumulation on the stent. More particularly, such systems are characterized by one or more devices that are integral structural portions of the stent and are RF or battery powered. Such a device may be configured to emit an ultrasonic wave at a determined frequency corresponding to the mechanical resonance of the stent. Alternatively or additionally, such a device or other portions of the stent may be configured with a coating that elutes a drug to minimizes plaque build up. However, in contrast with existing drug-eluting stents, a device of the present invention controllably releases the drug in response to commands from an externally-positioned device.

Such biocompatible devices may be configured similarly to the devices described in the commonly owned U.S. Pat. No. 6,164,284 (hereinafter referred to as the '284 patent), incorporated herein by reference in its entirety. Preferably, biocompatible devices of the present invention differ from those in the '284 patent in that instead of relying upon the use of an internal battery, e.g., rechargeable, the use of RF powering, e.g., as shown in common owned U.S. Pat. Nos. 5,193,539 and 5,193,540 (herein referred to as the '539 and '540 patents) each of which is incorporated herein by reference in their entirety, is used. This implementation is especially preferred due to the periodic use of the treatment described herein.

In accordance with the present invention, a preferred system for preventing restenosis following placement in a blood vessel of a patient is comprised of (1) an expandable wire mesh tube comprised of a plurality of integral lattice portions and configured for expansion within a blood vessel of a patient, and (2) an electrically-powered biocompatible device positioned as at least one of the integral lattice portions which is comprised of (a) a controller within the biocompatible device responsive to an externally-provided command signal, and (b) an ultrasonic emitter within said biocompatible device coupled to the controller for emitting an ultrasonic wave to induce mechanical vibrations in said wire mesh to thereby minimize forming of plaque on the stent.

In a further aspect of embodiments of the present invention, the externally-provided command signal may contain instructions to determine the frequency and/or the amplitude of the ultrasonic wave and this command signal may be generated by amplitude modulating an externally-provided AC magnetic field which provides operating power to the biocompatible structure.

In a still further aspect of the present invention, the biocompatible structure or other portion of the stent may alternatively or additionally have a drug-eluting coating on at least a portion of its surface and by passing current through this coating via at least two electrodes, the drug may be controllably released in response to a portion of the externally-provided command signal.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention is generally directed to systems and methods for preventing restenosis following a stent procedure by using an electrically-controlled biocompatible device under control of an externally-positioned control device that issues commands to the implanted device to use an electrically controlled signal to minimize plaque accumulation on the stent. More particularly, such systems are characterized by one or more devices that are integral structural portions of the stent and are RF or battery powered. Such a device may be configured to emit an ultrasonic wave at a determined frequency corresponding to the mechanical resonance of the stent. Alternatively or additionally such a device or other portions of the stent may be configured with a coating that elutes a drug to minimizes plaque build up. However, in contrast with existing drug-eluting stents, a device of the present invention controllably releases the drug in response to commands from an externally-positioned device.

Such biocompatible devices may be configured similarly to the devices described in the commonly owned U.S. Pat. No. 6,164,284 (hereinafter referred to as the '284 patent), incorporated herein by reference in its entirety. Preferably, biocompatible devices of the present invention differ from those in the '284 patent in that instead of relying upon the use of an internal battery, e.g., rechargeable, the use of RF powering, e.g., as shown in common owned U.S. Pat. Nos. 5,193,539 and 5,193,540 (herein referred to as the '539 and '540 patents) each of which is incorporated herein by reference in their entirety, is used. This implementation is especially preferred due to the periodic use of the treatment described herein. While, the biocompatible device of the present invention is in many ways a much simpler device that that described in the '284, '539, and '540 patents (permitting a smaller casing), the teachings of these patents are a useful background in understanding the present invention. Accordingly, for background purposes, the teachings of the '284 patent are now set forth.

Figure 1:
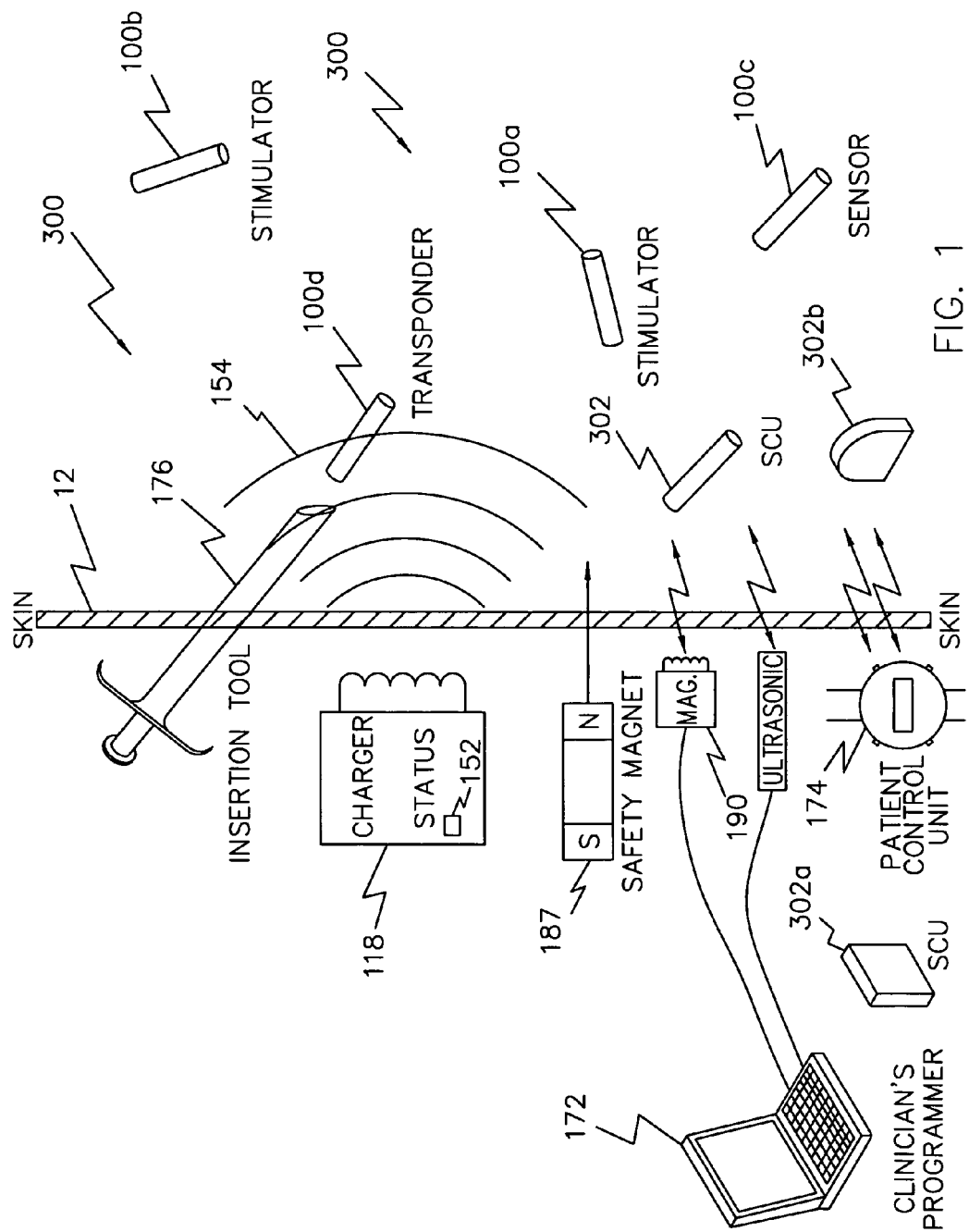
FIG. 1 is a simplified block diagram of an exemplary system suitable for practicing the present invention, the system being comprised of implanted devices, e.g., microstimulators, microsensors and microtransponders, under control of a system control unit (SCU).
Figure 2:
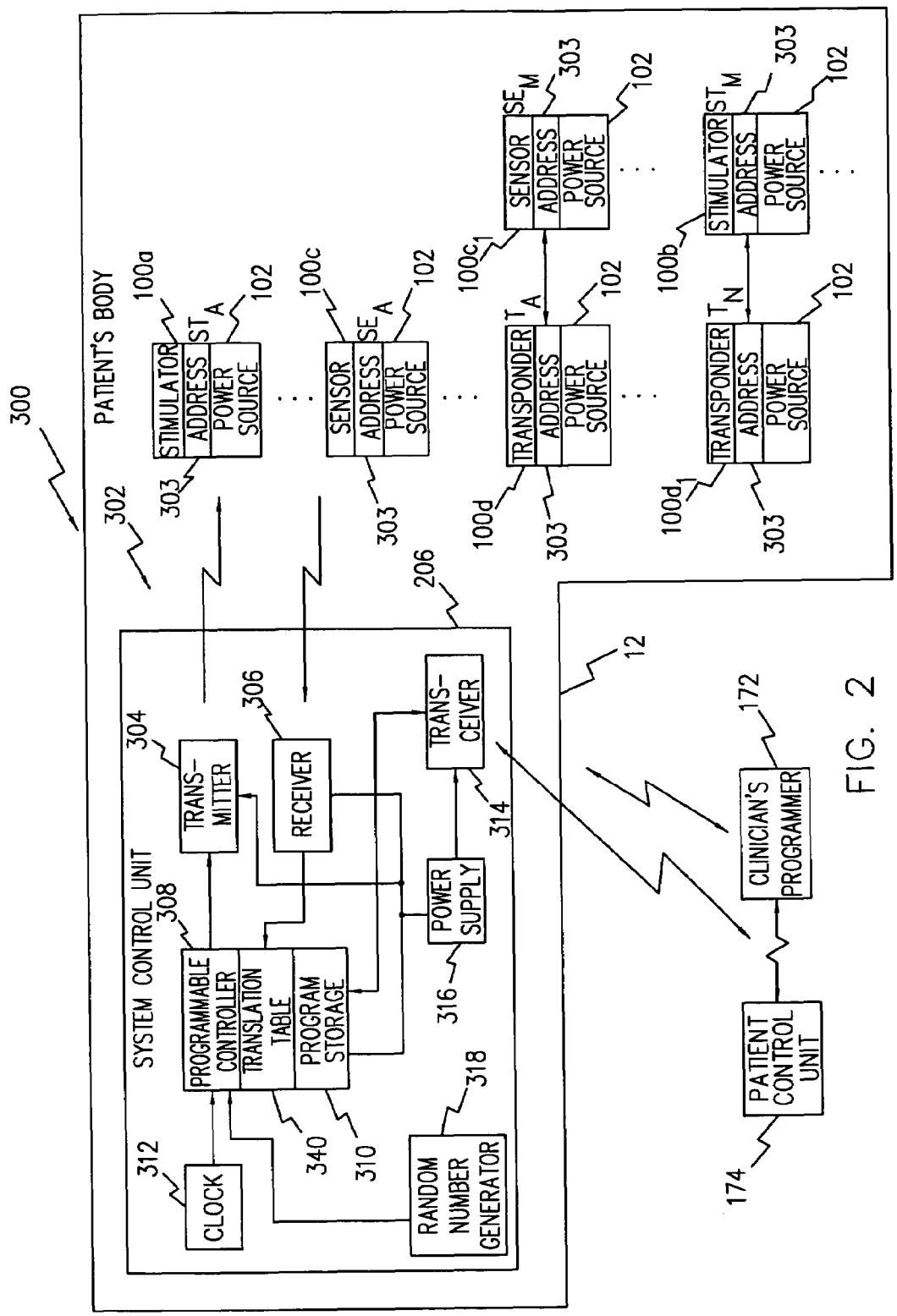
FIG. 2 comprises a block diagram of the system of FIG. 1 showing the functional elements that form the system control unit and implanted microstimulators, microsensors and microtransponders.

FIGS. 1 and 2 show an exemplary system 300 made of implanted devices 100 under control of a system control unit (SCU) 302, preferably also implanted beneath a patient's skin 12. As described in the '284 patent, potential implanted devices 100 (see also the block diagram shown in FIG. 3A) include stimulators, e.g., 100a and 100b, sensors, e.g., 100c, and transponders, e.g., 100d. The stimulators, e.g., 100a, can be remotely programmed to output a sequence of drive pulses to body tissue proximate to its implanted location via attached electrodes. The sensors, e.g., 100c, can be remotely programmed to sense one or more physiological or biological parameters in the implanted environment of the device, e.g., temperature, glucose level, $O_2$ content, nerve potential, muscle potential, etc. Transponders, e.g., 100d, are devices which can be used to extend the interbody communication range between stimulators and sensors and other devices, e.g., a clinician's programmer 172 and the patient control unit 174. Preferably, these stimulators, sensors and transponders are contained in sealed elongate housings having an axial dimension of less than 60 mm and a lateral dimension of less than 6 mm. Accordingly, such stimulators, sensors and transponders are respectively referred to as microstimulators, microsensors, and microtransponders or referred to in general as implantable stimulator/sensor devices. Such microstimulators and microsensors can thus be positioned beneath the skin 12 within a patient's body using a hypodermic type insertion tool 176.

As described in the '284 patent, microstimulators and microsensors are remotely programmed and interrogated via a wireless communication channel, e.g., modulated AC magnetic, sound (i.e., ultrasonic), RF or electric fields, typically originating from control devices external to the patient's body, e.g., the clinician's programmer 172 or patient control unit 174. Typically, the clinician's programmer 172 is used to program a single continuous or one time pulse sequence into each microstimulator and/or measure a biological parameter from one or more microsensors. Similarly, the patient control unit 174 typically communicates with the implanted devices 100, e.g., microsensors 100c, to monitor biological parameters. In order to distinguish each implanted device over the communication channel, each implanted device is manufactured with a unique address or identification code (ID) 303 specified in address storage circuitry 108 (see FIG. 3A) as described in the '284 patent. Unique is a relative term, e.g., the more bits used to specify the identification code the easier it will be to distinguish one device or, in the case of master devices, one system of devices from another system of devices. Accordingly, as used in this patent application, unique is only intended to specify that the ID 303 is distinguishable from the IDs of other devices that may exist within the same environment.

By using one or more such implantable devices in conjunction with the SCU 302, the capabilities of such implanted devices can be further expanded. For example, in an open loop mode (described below in reference to FIG. 4), the SCU 302 can be programmed to periodically initiate tasks, e.g., perform real time tasking, such as transmitting commands to microstimulators according to a prescribed treatment regimen or periodically monitor biological parameters to determine a patient's status or the effectiveness of a treatment regimen. Alternatively, in a closed loop mode (described below in reference to FIGS. 5-7), the SCU 302 may periodically interrogate one or more microsensors and accordingly adjust the commands transmitted to one or more microstimulators.

FIG. 2 shows a system 300 comprised of (1) one or more implantable devices 100 operable to sense and/or stimulate a patient's body parameter in accordance with one or more controllable operating parameters and (2) the SCU 302. The SCU 302 is primarily comprised of (1) a housing 206, preferably sealed and configured for implantation beneath the skin of the patient's body, e.g., as described in the '284 patent in reference to the implanted devices 100, (2) a signal transmitter 304 in the housing 206 for transmitting command signals, (3) a signal receiver 306 in the housing 206 for receiving status signals, and (4) a programmable controller 308, e.g., a microcontroller or state machine, in the housing 206 responsive to received status signals for producing command signals for transmission by the signal transmitter 304 to other implantable devices 100. The sequence of operations of the programmable controller 308 is determined by an instruction list, i.e., a program, stored in program storage 310, coupled to the programmable controller 308. While the program storage 310 can be a nonvolatile memory device, e.g., ROM, manufactured with a program corresponding to a prescribed treatment regimen, it is preferable that at least a portion of the program storage 310 be an alterable form of memory, e.g., RAM, EEPROM, etc., whose contents can be remotely altered as described further below. However, it is additionally preferable that a portion of the program storage 310 be nonvolatile so that a default program is always present. The rate at which the program contained within the program storage 310 is executed is determined by clock/oscillator 312. Additionally, a real time clock operating in response to clock/oscillator 312 preferably permits tasks to be scheduled at specified times of day.

The signal transmitter 304 and signal receiver 306 preferably communicate with implanted devices 100 using an RF signal, e.g., a propagated electromagnetic wave, modulated by a command data signal. Alternatively, an audio transducer may be used to generate mechanical vibrations having a carrier frequency modulated by a command data signal. In an exemplary embodiment, a carrier frequency of 100 kHz is used which corresponds to a frequency that freely passes through a typical body's fluids and tissues. However, such sound means that operate at any frequency, e.g., greater than 1 Hz, are also considered to be suitable for a potential communication channel. Alternatively, the signal transmitter 304 and signal receiver 306 can communicate using modulated AC, e.g., magnetic fields.

The clinician's programmer 172 and/or the patient control unit 174 and/or other external control devices can also communicate with the implanted devices 100, as described in the '284 patent, preferably using a modulated RF or AC magnetic field. Alternatively, such external devices can communicate with the SCU 302 via a transceiver 314 coupled to the programmable controller 308. Since, the signal transmitter 304 and signal receiver 306 may operate using a different communication means, a separate transceiver 314 which operates using an alternative communication means may be used for communicating with external devices. However, a single transmitter 304/receiver 306 can be used in place of transceiver 314 for communicating with the external devices and implanted devices if a common communication channel is used.

Figure 3A:
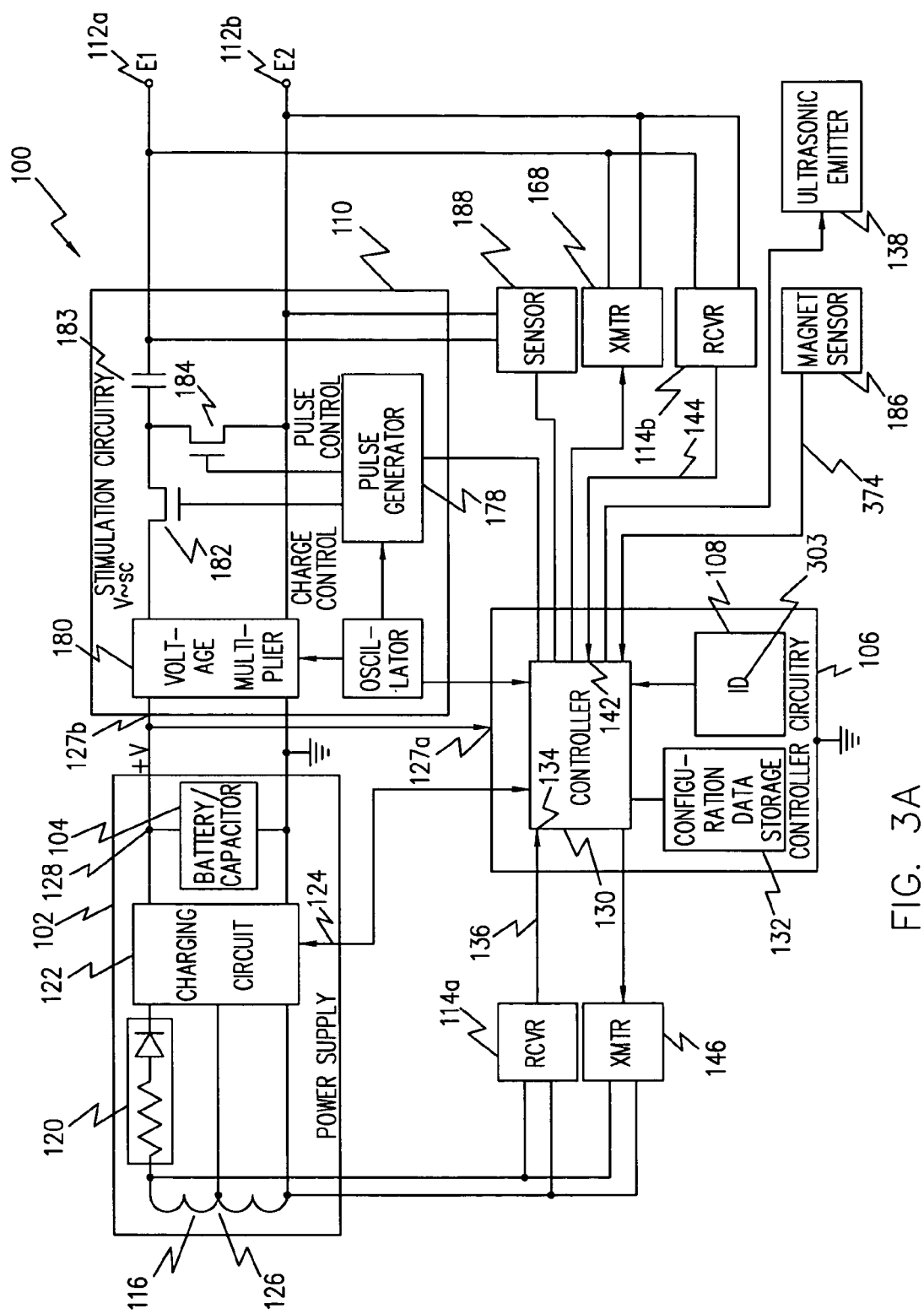
FIG. 3A comprises a block diagram of an exemplary implantable device, as shown in U.S. Pat. No. 6,164,284, including a battery for powering the device for a period of time in excess of one hour in response to a command from the system control unit.
Figure 3B:
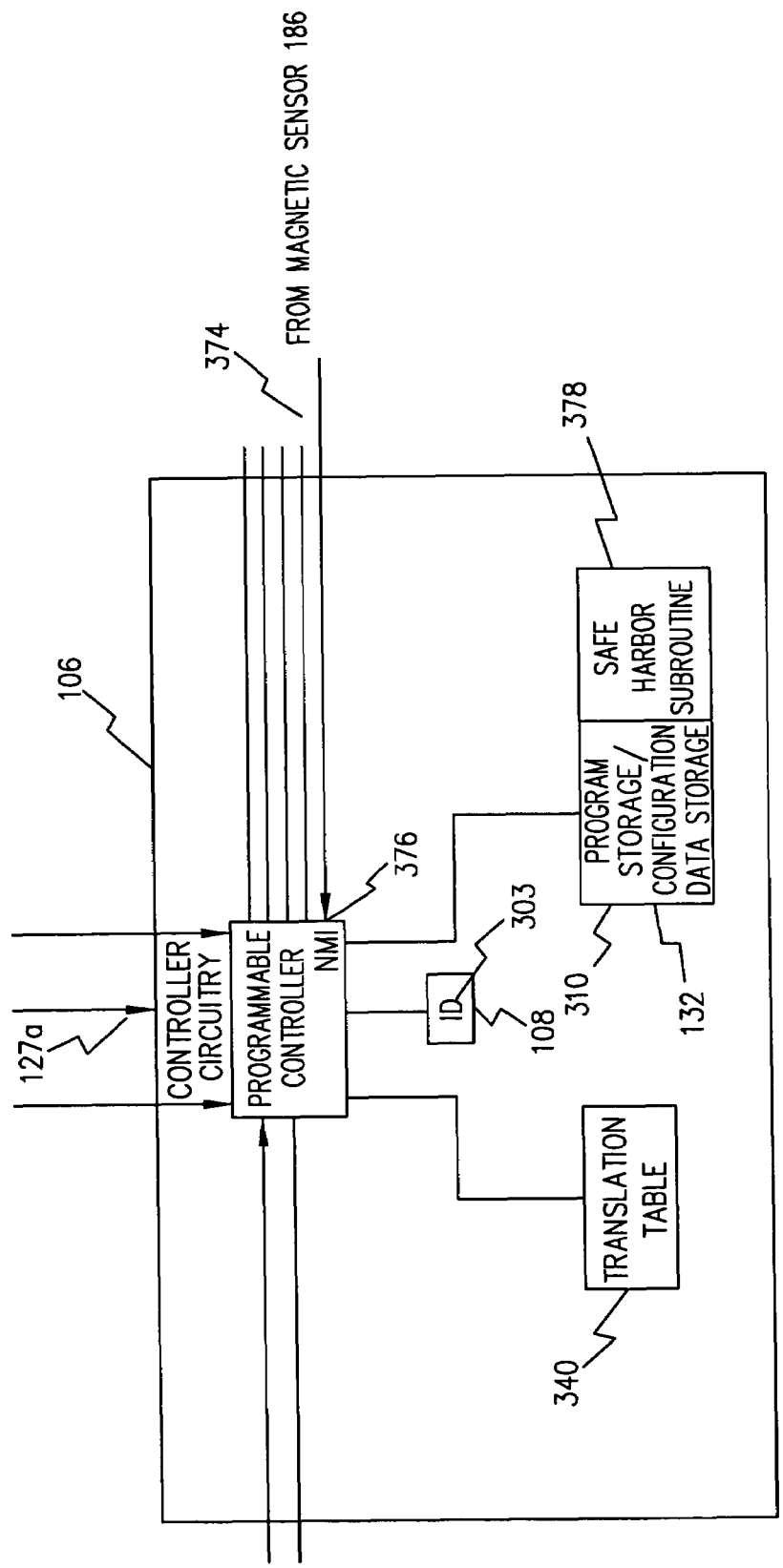
FIG. 3B comprises a simplified block diagram of controller circuitry that can be substituted for the controller circuitry of FIG. 3A, thus permitting a single device to be configured as a system control unit and/or a microstimulator and/or a microsensor and/or a microtransponder.

FIG. 3A comprises a block diagram of an exemplary implantable device 100 operable under control of controller circuitry 106 and includes a battery 104, preferably rechargeable, for powering the device for a period of time in excess of one hour and responsive to command signals from a remote master device, e.g., the SCU 302. The controller circuitry 106 is primarily comprised of a controller 130, configuration data storage 132 for prescribing its operation, and address storage circuitry 108 for storing the ID 303 of the device. As described in the '284 patent, the implantable device 100 is preferably configurable to alternatively operate as a microstimulator and/or microsensor and/or microtransponder due to the commonality of most of the circuitry contained within. Such circuitry may be further expanded to permit a common block of circuitry to also perform the functions required for the SCU 302. Accordingly, FIG. 3B shows an alternative implementation of the controller circuitry 106 of FIG. 3A that is suitable for implementing a microstimulator and/or a microsensor and/or a microtransponder and/or the SCU 302. In this implementation, the configuration data storage 132 can be alternatively used as the program storage 310 when the implantable device 100 is used as the SCU 302. In this implementation, XMTR 168 corresponds to the signal transmitter 304 and the RCVR 114b corresponds to the signal receiver 306 (preferably operable via electrodes 112a and 112b operating as an RF antenna) and the RCVR 114a and XMTR 146 correspond to the transceiver 314 (preferably operable via coil 116 for AC magnetic modes of communication).

Preferably, the contents of the program storage 310, i.e., the software that controls the operation of the programmable controller 308, can be remotely downloaded, e.g., from the clinician's programmer 172 using data modulated onto an RF signal or an AC magnetic field. In this mode, it is preferable that the contents of the program storage 310 for each SCU 302 be protected from an inadvertent change. Accordingly, the contents of the address storage circuitry 108, i.e., the ID 303, is preferably used as a security code to confirm that the new program storage contents are destined for the SCU 302 receiving the data. This feature is particularly significant if multiple patient's could be physically located, e.g., in adjoining beds, within the communication range of the clinician's programmer 172.

Preferably, the SCU 302 can operate for an extended period of time, e.g., in excess of one hour, from an internal power supply 316 (see FIG. 2). While a primary battery, i.e., a nonrechargeable battery, is suitable for this function, it is preferable that the power supply 316 include a rechargeable battery, e.g., battery 104 as described in the '284 patent, that can be recharged via an AC magnetic field produced external to the patient's body. Accordingly, power supply 102 of FIG. 3A is the preferred power supply 316 for the SCU 302 as well.

The battery-powered devices 100 of the '284 patent are preferably configurable to operate in a plurality of operational modes, e.g., via a communicated command signal. In a first operational mode, device 100 is remotely configured to be a microstimulator, e.g., 100a and 100b. In this embodiment (see FIG. 3A), controller 130 commands stimulation circuitry 110 to generate a sequence of drive pulses through electrodes 112 to stimulate tissue, e.g., a nerve or muscle, proximate to the implanted location of the microstimulator, e.g., 100a or 100b. In operation, a programmable pulse generator 178 and voltage multiplier 180 are configured with parameters corresponding to a desired pulse sequence and specifying how much to multiply (or divide) the battery voltage (e.g., by summing charged capacitors or similarly charged battery portions) to generate a desired compliance voltage $V_c$. A first FET 182 is periodically energized to store charge into capacitor 183 (in a first direction at a low current flow rate through the body tissue) and a second FET 184 is periodically energized to discharge capacitor 183 in an opposing direction at a higher current flow rate which stimulates a nearby muscle or nerve. Alternatively, electrodes can be selected that will form an equivalent capacitor within the body tissue.

In a next operational mode, the battery-powered implantable device 100 can be configured to operate as a microsensor, e.g., 100c, that can sense one or more physiological or biological parameters in the implanted environment of the device. In accordance with a preferred mode of operation, the system control unit 302 periodically requests the sensed data from each microsensor 100c using its ID 303 stored in the address storage circuitry 108, and responsively sends command signals to microstimulators, e.g., 100a and 100b, adjusted according to the sensed data. For example, sensor circuitry 188 can be coupled to the electrodes 112 to sense or otherwise used to measure a biological parameter, e.g., temperature, glucose level, $O_2$ content, voltage, current, impedance, etc., and provide the sensed data to the controller circuitry 106. Preferably, the sensor circuitry 188 includes a programmable bandpass filter and an analog to digital (A/D) converter that can sense and accordingly convert the voltage levels across the electrodes 112 into a digital quantity. Alternatively, the sensor circuitry 188 can include one or more sense amplifiers to determine if the measured voltage exceeds a threshold voltage value or is within a specified voltage range. Furthermore, the sensor circuitry 188 can be configurable to include integration circuitry to further process the sensed voltage. The operational mode of the voltage sensor circuitry 188 is remotely programmable via the device's communication interface.

Additionally, the sensing capabilities of a microsensor preferably include the capability to monitor the battery status via path 124 from the charging circuit 122 and can additionally include using an ultrasonic transducer, i.e., emitter/receiver, (not shown) or the coil 116 to respectively measure the ultrasonic, magnetic or propagated RF signal magnitudes (or communication time delays) of signals transmitted between a pair of implanted devices and thus determine the relative locations of these devices. This information can be used to determine the amount of body movement, e.g., the amount that an elbow or finger is bent, and thus form a portion of a closed loop motion control system.

In another operational mode, the battery-powered implantable device 100 can be configured to operate as a microtransponder, e.g., 100d. In this operational mode, the microtransponder receives (via the aforementioned RCVR 114a using AC magnetic, sonic, RF, or electric communication modes) a first command signal from the SCU 302 and retransmits this signal (preferably after reformatting) to other implanted devices (e.g., microstimulators, microsensors, and/or microtransponders) using the aforementioned XMTR 168 using magnetic, sonic, RF or electric communication modes. While a microtransponder may receive one mode of command signal, e.g., magnetic, it may retransmit the signal in another mode, e.g., RF. For example, clinician's programmer 172 may emit a modulated magnetic signal using a magnetic emitter 190 (see FIG. 1) to program/command the implanted devices 100. However, the magnitude of the emitted signal may not be sufficient to be successfully received by all of the implanted devices 100. As such, a microtransponder 100d may receive the modulated magnetic signal and retransmit it (preferably after reformatting) as a modulated ultrasonic or RF signal which can pass through the body with fewer restrictions. In another exemplary use, the patient control unit 174 may need to monitor a microsensor 100c in a patient's foot. Despite the efficiency of ultrasonic, magnetic and propagated RF communication in a patient's body, such a signal could still be insufficient to pass from a patient's foot to a patient's wrist (the typical location of the patient control unit 174). As such, a microtransponder 100d could be implanted (if needed) in the patient's torso to improve the communication link.

Figure 4:
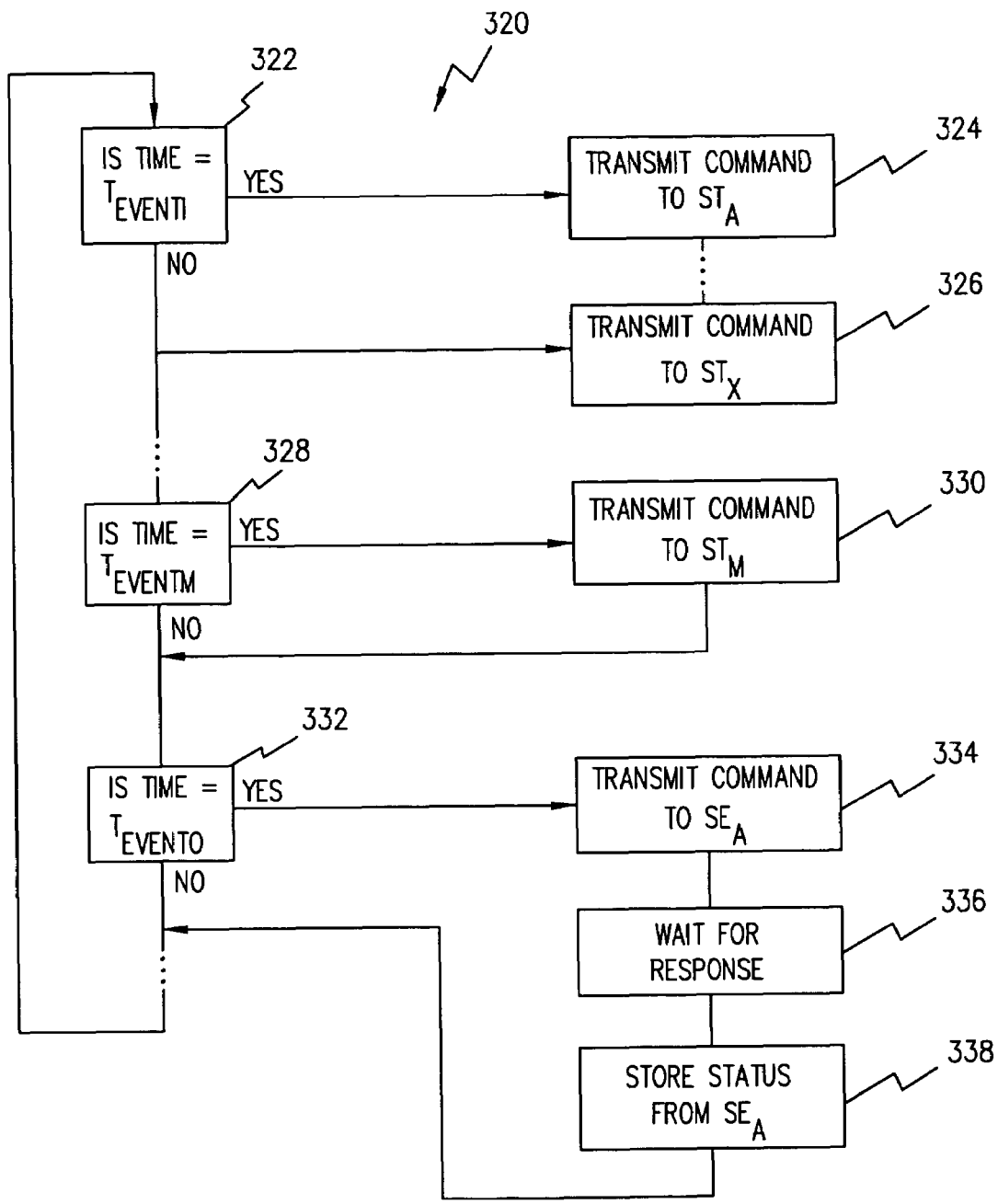
FIG. 4 shows an exemplary flow chart of the use of an exemplary system in an open loop mode for controlling/monitoring a plurality of implanted devices, e.g., microstimulators, microsensors.

FIG. 4 shows a block diagram of an exemplary open loop control program, i.e., a task scheduler 320, for controlling/monitoring a body function/parameter. In this process, the programmable controller 308 is responsive to the clock 312 (preferably a crystal controlled oscillator to thus permit real time scheduling) in determining when to perform any of a plurality of tasks. In this exemplary flow chart, the programmable controller 308 first determines in block 322 if it is now at a time designated as $T_{EVENT1}$ (or at least within a sampling error of that time), e.g., at 1:00 AM. If so, the programmable controller 308 transmits a designated command to microstimulator A ($ST_A$) in block 324. In this example, the control program continues where commands are sent to a plurality of stimulators and concludes in block 326 where a designated command is sent to microstimulator X ($ST_X$). Such a subprocess, e.g., a subroutine, is typically used when multiple portions of body tissue require stimulation, e.g., stimulating a plurality of muscle groups in a paralyzed limb to avoid atrophy. The task scheduler 320 continues through multiple time event detection blocks until in block 328 it determines whether the time $T_{EVENTM}$ has arrived. If so, the process continues at block 330 where, in this case, a single command is sent to microstimulator M ($ST_M$). Similarly, in block 332 the task scheduler 320 determines when it is the scheduled time, i.e., $T_{EVENTO}$, to execute a status request from microsensor A ($SE_A$). If so, a subprocess, e.g., a subroutine, commences at block 334 where a command is sent to microsensor A ($SE_A$) to request sensor data and/or specify sensing criteria. Microsensor A ($SE_A$) does not instantaneously respond. Accordingly, the programmable controller 308 waits for a response in block 336. In block 338, the returned sensor status data from microsensor A ($SE_A$) is stored in a portion of the memory, e.g., a volatile portion of the program storage 310, of the programmable controller 308. The task scheduler 320 can be a programmed sequence, i.e., defined in software stored in the program storage 310, or, alternatively, a predefined function controlled by a table of parameters similarly stored in the program storage 310. A similar process may be used where the SCU 302 periodically interrogates each implantable device 100 to determine its battery status.

Figure 5:
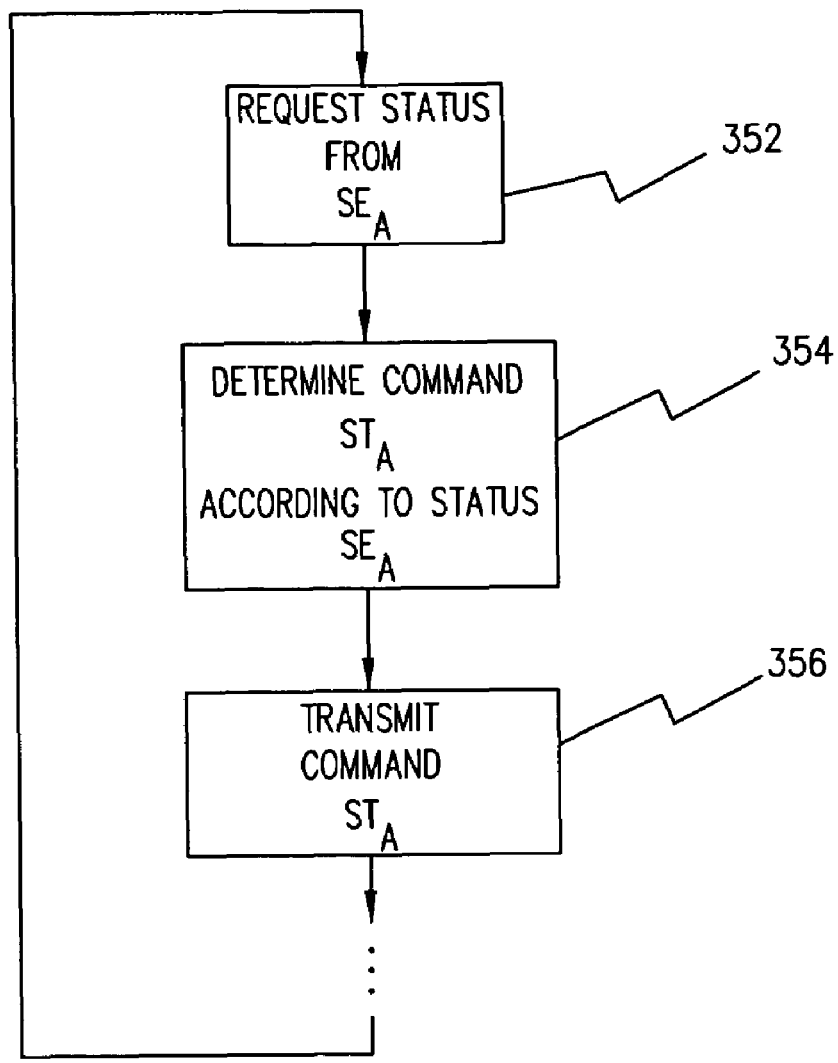
FIG. 5 shows a simplified flow chart of the use of closed loop control of a microstimulator by altering commands from the system control unit in response to status data received from a microsensor.

FIG. 5 is an exemplary block diagram showing the use of such a system to perform closed loop control of a body function. In block 352, the SCU 302 requests status from microsensor A ($SE_A$). The SCU 302, in block 354, then determines whether the present command given to a microstimulator is satisfactory and, if necessary, determines a new command and transmits the new command to the microstimulator A ($ST_A$) in block 356. For example, if microsensor A ($SE_A$) is reading a voltage corresponding to the degree of contraction resulting from stimulating a muscle, the SCU 302 could transmit a command to microstimulator A ($ST_A$) to adjust the sequence of drive pulses, e.g., in magnitude, duty cycle, etc., and accordingly change the voltage sensed by microsensor A ($SE_A$). Accordingly, closed loop, i.e., feedback, control is accomplished. The characteristics of the feedback (proportional, integral, derivative (PID)) control are preferably program controlled by the SCU 302 according to the control program contained in program storage 310.

Figure 6:
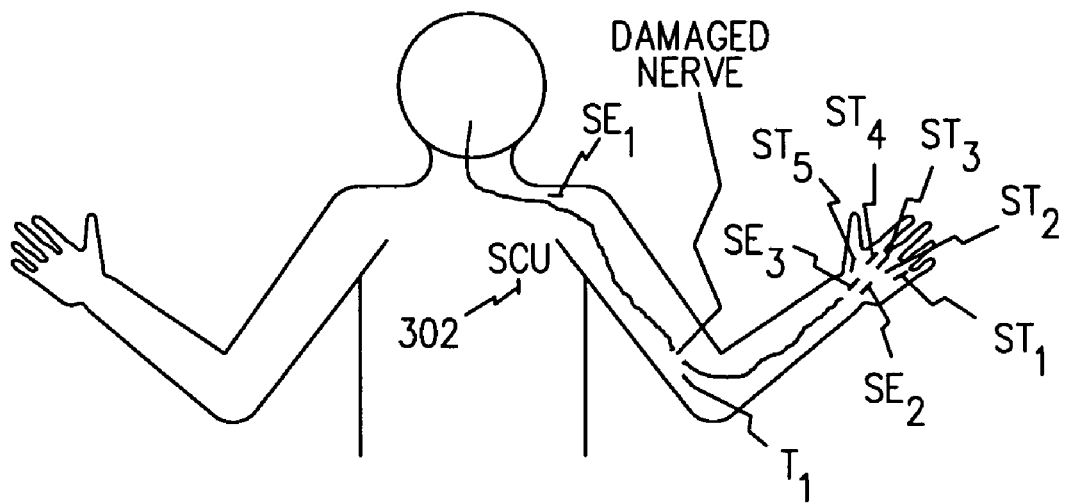
FIG. 6 shows an exemplary injury, i.e., a damaged nerve, and the placement of a plurality of implanted devices, i.e., microstimulators, microsensors and a microtransponder under control of the system control unit for "replacing" the damaged nerve.

FIG. 6 shows an exemplary injury treatable by such a system 300. In this exemplary injury, the neural pathway has been damaged, e.g., physically or effectively (as a consequence of a stroke or the like) severed, just above the patient's left elbow. The goal of this exemplary system is to bypass the damaged neural pathway to permit the patient to regain control of the left hand. An SCU 302 is implanted within the patient's torso to control a plurality of stimulators, $ST_1$-$ST_5$, implanted proximate to the muscles respectively controlling the patient's thumb and fingers (shown in the patient's hand for simplicity). Additionally, microsensor 1 ($SE_1$) is implanted proximate to an undamaged nerve portion where it can sense a signal generated from the patient's brain when the patient wants hand closure. Optional microsensor 2 ($SE_2$) is implanted in a portion of the patient's hand where it can sense a signal corresponding to stimulation/motion of the patient's pinky finger and microsensor 3 ($SE_3$) is implanted and configured to measure a signal corresponding to grip pressure generated when the fingers of the patient's hand are closed. Additionally, an optional microtransponder ($T_1$) is shown which can be used to improve the communication between the SCU 302 and the implanted devices.

Figure 7:
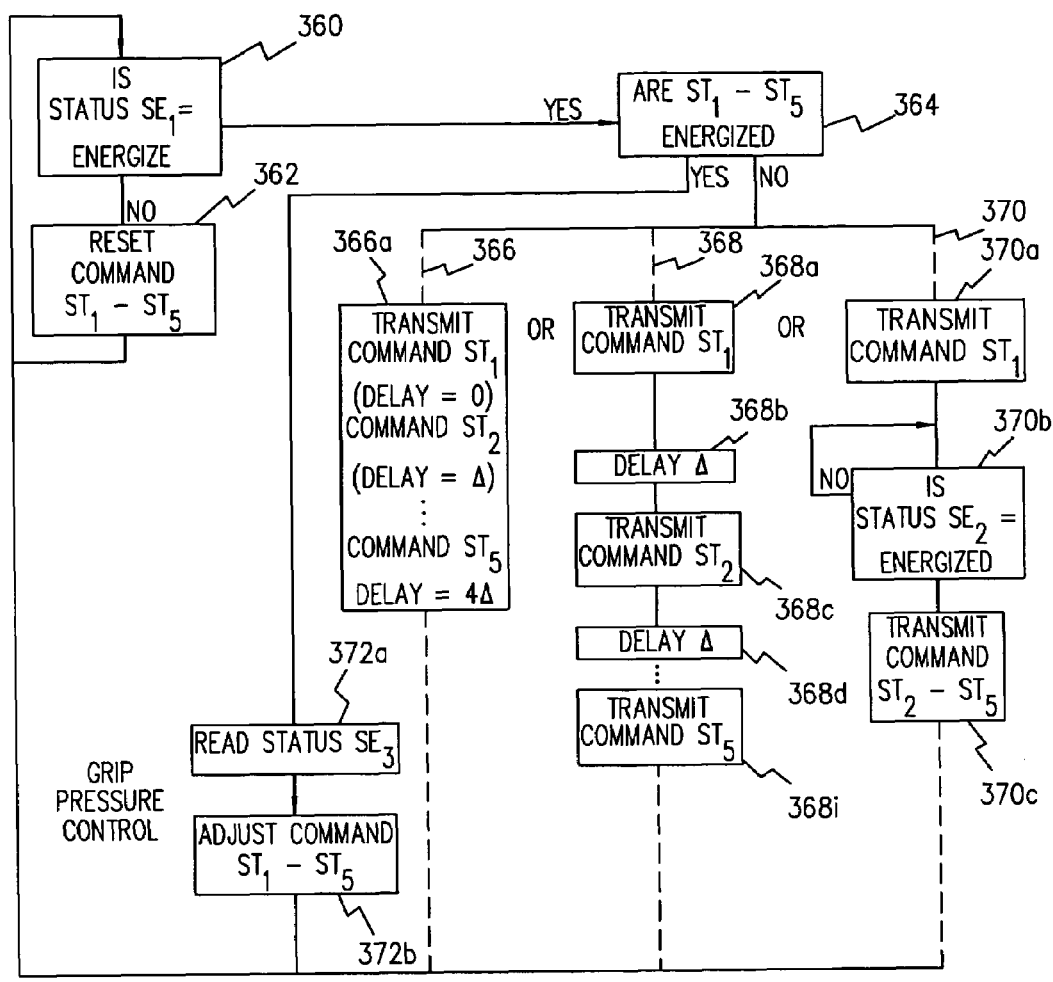
FIG. 7 shows a simplified flow chart of the control of the implanted devices of FIG. 6 by the system control unit.

FIG. 7 shows an exemplary flow chart for the operation of the SCU 302 in association with the implanted devices in the exemplary system of FIG. 6. In block 360, the SCU 302 interrogates microsensor 1 ($SE_1$) to determine if the patient is requesting actuation of his fingers. If not, a command is transmitted in block 362 to all of the stimulators ($ST_1$-$ST_5$) to open the patient's hand, i.e., to de-energize the muscles which close the patient's fingers. If microsensor 1 ($SE_1$) senses a signal to actuate the patient's fingers, the SCU 302 determines in block 364 whether the stimulators $ST_1$-$ST_5$ are currently energized, i.e., generating a sequence of drive/stimulation pulses. If not, the SCU 302 executes instructions to energize the stimulators. In a first optional path 366, each of the stimulators is simultaneously (subject to formatting and transmission delays) commanded to energize in block 366a. However, the command signal given to each one specifies a different start delay time. Accordingly, there is a stagger between the actuation/closing of each finger.

In a second optional path 368, the microstimulators are consecutively energized by a delay Δ. Thus, microstimulator 1 ($ST_1$) is energized in block 368a, a delay is executed within the SCU 302 in block 368b, and so on for all of the microstimulators. Accordingly, paths 366 and 368 perform essentially the same function. However, in path 366, the interdevice timing is performed by the clocks within each implanted device 100 while in path 368, the SCU 302 is responsible for providing the interdevice timing.

In path 370, the SCU 302 actuates a first microstimulator ($ST_1$) in block 30a and waits in block 30b for its corresponding muscle to be actuated, as determined by microsensor 2 ($SE_2$), before actuating the remaining stimulators ($ST_2$-$ST_5$) in block 370c. This implementation could provide more coordinated movements in some situations.

Once the stimulators have been energized, as determined in block 364, closed loop grip pressure control is performed in blocks 372a and 372b by periodically reading the status of microsensor 3 ($SE_3$) and adjusting the commands given to the stimulators ($ST_1$-$ST_5$) accordingly. Consequently, this exemplary system has enabled the patient to regain control of his hand including coordinated motion and grip pressure control of the patient's fingers.

Referring again to FIG. 3A, a magnetic sensor 186 is shown. In the '284 patent, it was shown that such a sensor 186 could be used to disable the operation of an implanted device 100, e.g., to stop or otherwise alter the operation of such devices in an emergency situation, in response to a DC magnetic field, preferably from an externally-positioned safety magnet 187 (see FIG. 1). Additionally, it is noted that power to at least some portions of a preferred implantable device may be removed when a magnetic field is sensed and thus power may be conserved. The magnetic sensor 186 can be implemented using various devices. Exemplary of such devices are devices manufactured by Nonvolatile Electronics, Inc. (e.g., their AA, AB, AC, AD, or AG series), Hall effect sensors, magnetoresistive sensors, and subminiature reed switches. Such miniature devices are configurable to be placed within the housing of the SCU 302 and implantable devices 100. While essentially passive magnetic sensors, e.g., reed switches, are possible, the remaining devices may include active circuitry that consumes power during detection of the DC magnetic field. Accordingly, it is preferred that controller circuitry 302 periodically, e.g., once a second, provide power to the magnetic sensor 186 and sample the magnetic sensor's output signal 374 during that sampling period. Additionally, a magnetoresistive sensor is especially preferred due to its small size that enables its use within the preferred implantable device 100 while conserving the available internal package volume. Furthermore, as described below, such sensors may be used as a proximity sensor which may be used to provide sequencing information to the system controller, e.g., the SCU 302.

The battery 104 used for powering the implantable device 100 (or SCU 302) is made from appropriate materials so as to preferably provide a power capacity of at least 1 microwatt-hour. Preferably, such a battery, e.g., a Li-I battery, has an energy density of about 240 mw-Hr/cm$^3$. The battery voltage V of an exemplary battery is nominally 3.6 volts, which is more than adequate for operating the CMOS circuits preferably used to implement the IC chip(s) 216, and/or other electronic circuitry, within the SCU 302.

The battery 104 may take many forms, any of which may be used so long as the battery can be made to fit within the small volume available. The battery 104 may be either a primary battery or a rechargeable battery. A primary battery offers the advantage of not requiring a recharging circuit and the disadvantage of not being rechargeable (which means once its energy has been used up, the implanted device no longer functions).

A preferred system for practicing the present invention is comprised of an implanted SCU 302 and a plurality of implanted devices 100, each of which contains its own rechargeable battery 104. As such, a patient is essentially independent of any external apparatus between battery chargings (which generally occur no more often than once an hour and preferably no more often than once every 24 hours). However, for some treatment regimens, it may be adequate to use a power supply analogous to that described in U.S. Pat. No. 5,324,316 that only provides power while an external AC magnetic field is being provided, e.g., from charger 118. Additionally, it may be desired, e.g., from a cost or flexibility standpoint, to implement the SCU 302 as an external device, e.g., within a watch-shaped housing that can be attached to a patient's wrist in a similar manner to the patient control unit 174.

The power consumption of the SCU 302 is primarily dependent upon the circuitry implementation, preferably CMOS, the circuitry complexity and the clock speed. For a simple system, a CMOS implemented state machine will be sufficient to provide the required capabilities of the programmable controller 308. However, for more complex systems, e.g., a system where an SCU 302 controls a large number of implanted devices 100 in a closed loop manner, a microcontroller may be required. As the complexity of such microcontrollers increases (along with its transistor count), so does its power consumption. Accordingly, a larger battery having a capacity of 1 to 10 watt-hours is preferred. While a primary battery is possible, it is preferable that a rechargeable battery be used. Such larger batteries will require a larger volume and accordingly, cannot be placed in the injectable housing described above.

Since only one SCU is required to implement a system, the battery life of the SCU may be accommodated by increasing the casing size (e.g., increasing at least one dimension to be in excess of 1 inch) for the SCU to accommodate a larger sized battery and either locating a larger SCU 302a (see FIG. 1) external to patient's body or a larger SCU 302b may be surgically implanted.

Essentially, there have been described two classes of implantable devices 100, a first which is typically referred to as being RF powered, i.e., it does not contain a battery but instead receives all of its operating power from an externally provided AC magnetic field (which field is preferably modulated to additionally wirelessly communicate commands to the implantable devices 100), and a second class which is referred to as battery powered which is powered by an internally provided battery which, in turn, is preferably rechargeable and periodically recharged by a similar externally provided magnetic field (see, for example, commonly assigned US Patent Application Publication No. 2003/0078634, which is incorporated herein by reference in its entirety, which describes recharging environments and techniques for use with such implantable devices) but preferably receives its wireless commands via a modulated RF signal. Thus, in this case, the wireless command signal may be distinct from the wireless charging signal. However, in most other ways, these two classes of implantable devices are similar, e.g., they have similar size restrictions, are suitable for implantation via injection, and can similarly stimulate neural pathways and, thus, they are accordingly generally interchangeable. However, due to the periodic use of the present invention, it is presently preferred that the biocompatible device more closely mimic the power supply functionality of a '539/'540 type devices which use an externally supplied AC magnetic field to charge an internal capacitor to subsequently power its internal electronic while implementing portions of the '284 type device to increase its functionality. However, it is recognized that the biocompatible device of the present invention generally requires less functionality than either of these devices and accordingly may be formed in a smaller casing.

Figure 8:
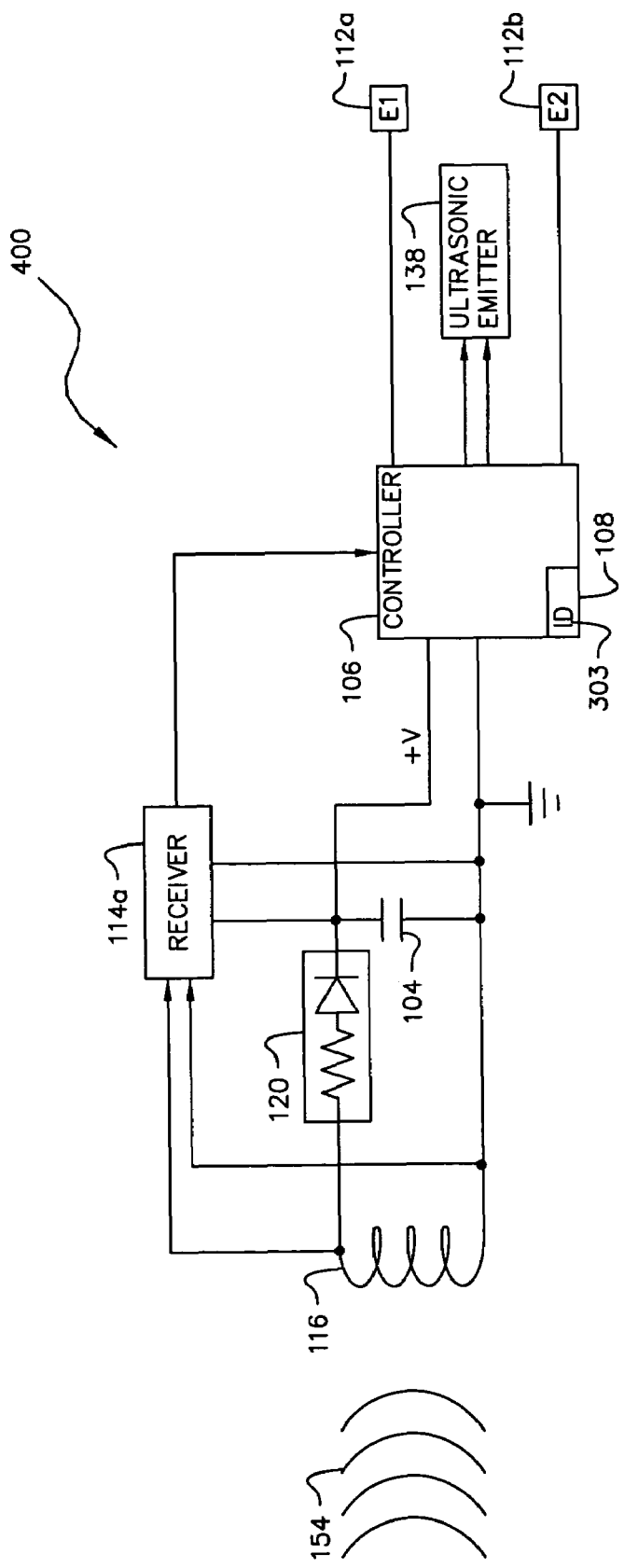
FIG. 8 shows a simplified block diagram of an exemplary implementation of a biocompatible device 400 of the present invention. Depending upon the embodiment of the present invention, subsets of this block diagram (which are derivative of that shown in FIG. 3A) may be used and other portions may be absent allowing its package size to be further decreased.

Accordingly, FIG. 8 shows a simplified block diagram of an exemplary implementation of a biocompatible device 400 of the present invention. It is also recognized that, depending upon the embodiment of the present invention, subsets of this block diagram (which are derivative of that shown in FIG. 3A) may be used and other portions may be absent (again, allowing its package size to be further decreased). Basically, in response to an externally provided AC magnetic field 154, a voltage is induced into coil 116 which is rectified, e.g., half-wave rectified, by rectifier 120 to produce an operating voltage +V across capacitor 104 which in turn is used to provide operating power to the device 400, primarily its controller 106 and RCVR 114a. Preferably, the AC magnetic field 154 is modulated with data from an external controller 406 (alternatively, a modulated RF signal may be used). RCVR 114a demodulates this AC magnetic field 154 and provides a data stream 420 to controller 106. This data is used to determine the operation of the controller 106 and in particular, the frequency and/or amplitude of the signal used to drive an ultrasonic emitter 138, e.g., a piezoelectric device or the like. The ultrasonic driver circuitry may be considered to be integral to the ultrasonic emitter 138 or the controller 106.

Figure 9:
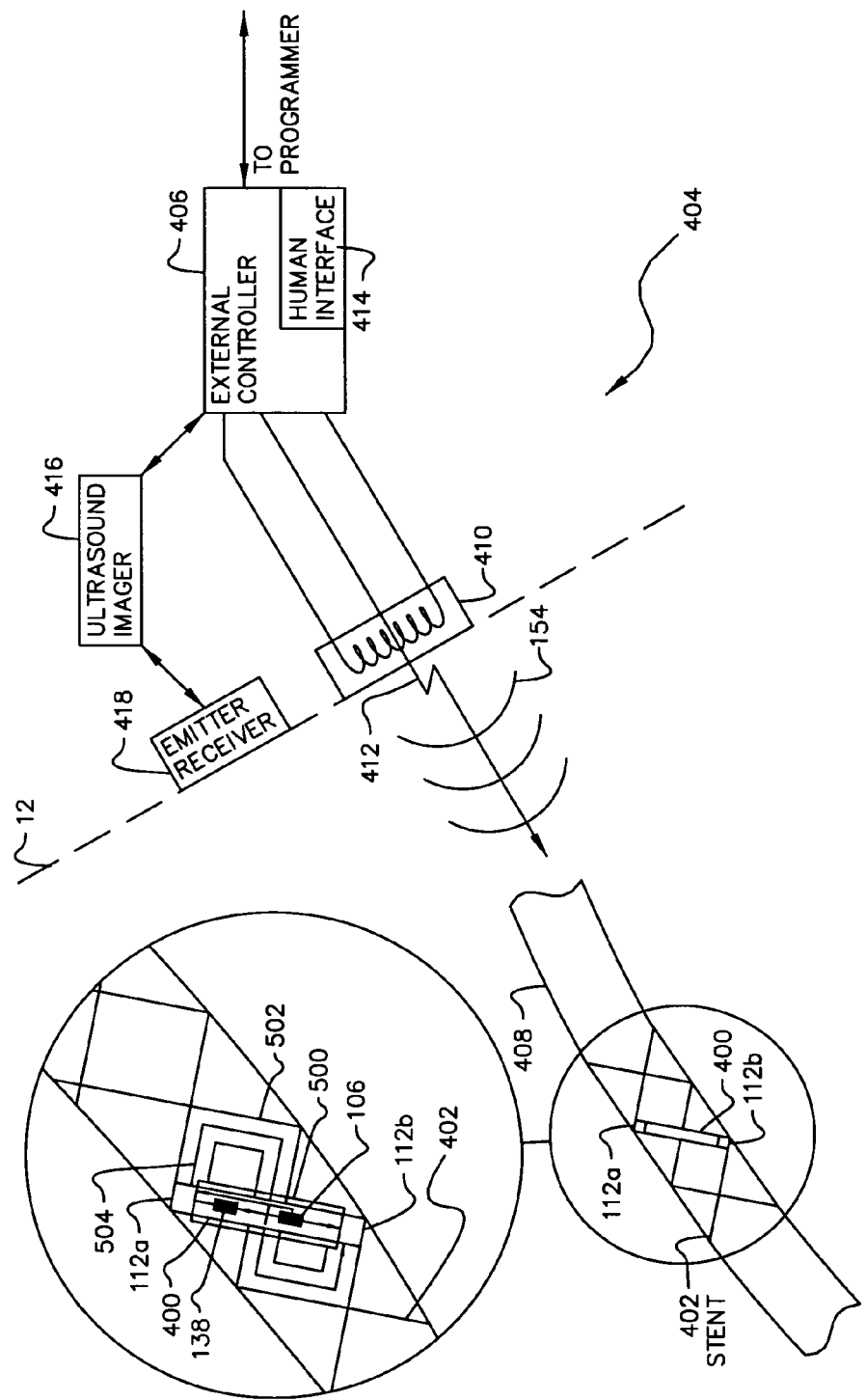
FIG. 9 shows an exemplary system of a stent having a biocompatible device portion that is responsive to commands from an external controller to cause the biocompatible portion to periodically emit ultrasonic energy to cause the implanted stent to mechanically vibrate to minimize plaque accumulation on the stent. Alternatively or additionally, the biocompatible device portion may responsively cause a steroid-eluting portion to controllably release a drug to minimize plaque accumulation.

[0052] As shown in the exemplary system 404 of FIG. 9, the controller circuitry 106 within the biocompatible device 400 portion of the stent 402 of the present invention (implanted within a patient's vessel 408 needing treatment, for example, a blood vessel such as a coronary artery), under control of commands from an external controller 406, e.g., patient control unit 174, clinician's programmer 172, an external SCU 302a, etc., is commanded, e.g., in a manner analogous to that described in relation to FIGS. 4-7, to emit the ultrasonic vibrations having programmable attributes, e.g., amplitude and/or frequency, etc., such that its ultrasonic emissions occur at the stent's mechanical resonance frequency to minimize plaque accumulation on the stent 402. The mechanical resonance of the stent 402 is essentially an inherent attribute of the stent 402 (somewhat effected by its environment, i.e., blood flow, blood/tissue density, and surrounding tissue). Accordingly, it is anticipated that an initial estimate of the resonant frequency may be determined from experimentation and may be used in future implantations. Similarly, the initial value for the desired amplitude level may be experimentally determined and then used in future implantations. Additionally, driver circuitry may also be included, e.g., within the controller 106 to drive a pair of electrodes 112 which may be used to cause a steroid eluting coating to be controllably released from the stent 402. In a system where this is the only remotely controllable device, an ID 303 is not necessary, i.e., the receipt of power and a control signal is sufficient to control a single device. However, in more complex systems, e.g., as described above in relation to the '284 patent, additional remotely controllable devices may be used to stimulate body tissue or sense body parameters. Accordingly, in such systems, the ID 303 within address storage circuitry 108 is used to selectively control the ultrasonic emissions and/or steroid eluting functions of the stent 402 of the present invention.

The purpose of the present invention is to minimize plaque accumulation on the stent 402 via the use of induced ultrasonic mechanical vibrations. While the risk is slight of an adverse reaction to removing any plaque accumulation from the stent 402 (especially if the present invention is used on a periodic basis, e.g., yearly, bi-annually) is minimal, it is presently not desired that these induced mechanical vibrations occur without supervision by a medical practitioner. Additionally, since it is presently preferred that this treatment occur periodically under medical supervision, an RF powered implantable device is the presently preferred device, i.e., a device that temporarily stores its operating power received from an externally provided magnetic field 154 that is induced into its internal coil 116 and then into a capacitor 104 used in place of the battery of the '284 patent. External controller 406 is coupled to an external coil 410 that is mounted via a harness (not shown) outside of the patient's body, i.e., skin 12, proximate to the implantation location of the stent 402. The external controller 406 preferably generates an alternating magnetic field 154 in coil 410 via an alternating current provided to the coil 410. Additionally, as described in relation to the '539/'540 patents, the alternating magnetic field is preferably amplitude modulated with control data that is addressable to control an individual biocompatible device 400 and its functions, e.g., frequency, amplitude, etc. Alternatively, as described in the '284 patent, the control data may be provided via a modulated RF field 412. Accordingly, while a common external controller 406 is shown for providing power and control information to the biocompatible device 400, it is recognized that a first device, e.g., charger 118, may provide power via an alternating magnetic field 154 and a second device, e.g., patient control unit 174, clinician's programmer 172, SCU 302*a*, etc., may provide the control information via another mode of communication, e.g., a modulated RF field 412. The programmed parameters or programming range may be entered through a human interface 414, e.g., a keyboard/display integral to the controller 406, or may be connected to a programming device, e.g., the clinician's programmer 172, a conventional PC, or the like.

Various clinical techniques, e.g., use of an ultrasound imager, may be used to confirm and/or maximize the efficacy of treatment with the present invention. Preferably, embodiments of the present invention integrate these techniques with the controller 406. Accordingly, an ultrasonic imager 416 and its associated emitter/receiver 418 may be coupled to the controller 406. By measuring the ultrasonic energy emitted from the stent 402, as an indication of whether the resonance of the stent 402 has been determined, a closed loop algorithm can be executed that alters the parameters programmed into the biocompatible device 400 and thus maximize the efficacy of the treatment (and/or determine the extent of the treatment required).

Figure 10:
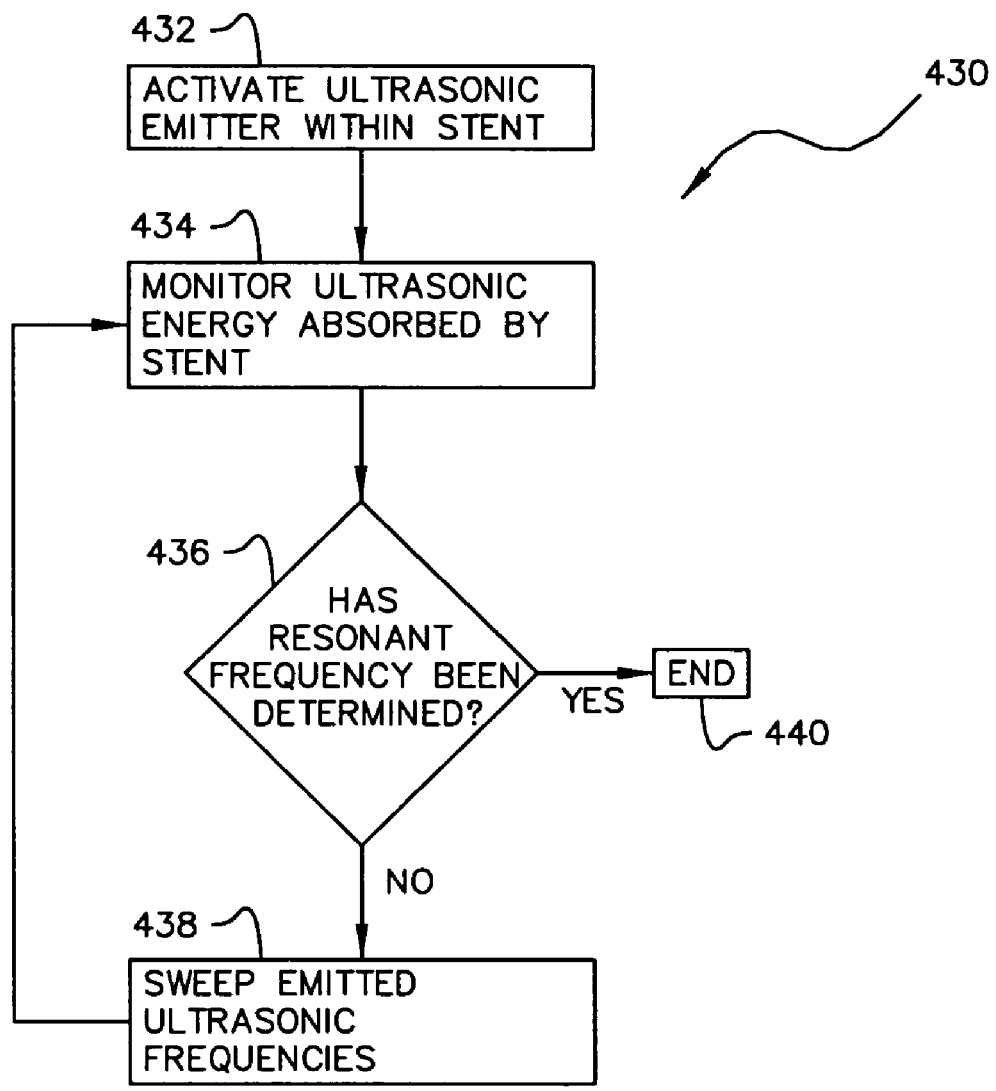
FIG. 10 shows an exemplary flow chart of an automated system for determining the selectable parameters, e.g., frequency and amplitude, of the ultrasonic emission by the biocompatible device portion of the stent of the present invention under control of an external programmer.

FIG. 10 shows an exemplary flow chart 430 of an automated system 404 for determining the selectable parameters, e.g., frequency and/or amplitude, of the ultrasonic signal emitted by the biocompatible device 400 that is an integral portion of the stent 402 of the present invention under control of the external controller/programmer 406. In embodiments of the present invention, the frequency of the emitted ultrasonic signal waves is adjusted to correspond to the determined resonant frequency of the implanted stent 402.

Initially in block 432, the ultrasonic emitter 138 of the integral biocompatible device 400 is activated by its internal controller 106 under control of the external controller 406. Initially, the frequency is set to a predetermined estimate, e.g., based on experience or a theoretical estimate of the resonant frequency of the stent 402. In block 434, an ultrasonic imager 416 begins monitoring the ultrasonic energy level emitted by the stent 402. In block 436, the inquiry is done as to whether the resonant frequency has been found. To make this determination, the emitted ultrasonic frequency is swept through a range of anticipated resonant frequencies in block 438, preferably in incremental steps, and the process iteratively repeats at block 434. Typically, the initial frequency selected in block 432 is below any anticipated resonant frequency and the frequencies incrementally sweep in block 438 upwards. Clearly, the converse may also occur, i.e., starting at a maximum anticipated frequency and sweeping downwards. Other possibilities also exist, e.g., starting at a predicted frequency with frequency sweeps up and down, etc. Once the resonant frequency has been determined, the process is completed in block 440 and this frequency is typically retained in the external programmer 406 and transferred as needed to the integral biocompatible device 400.

Additionally, it may be desired to coat the stent with a high Q value material to maximize the mechanical vibration of the stent 402. For example, the stent may be fabricated from a nickel-titanium alloy, such as Nitinol or another shape-memory alloy. It may then be desirable to coat the internal diameter and/or the external diameter with a Titanium 6Al-4V which is known to have a Q value of about 20,000. For comparison purposes, low carbon steel has a Q of about 250, polycarbonate has a Q of about 100 and aluminum has a Q of about 10,000. Therefore, it may be desirable to "adjust" the characteristics of mechanical vibration to optimize the shedding of any plaque reformation. Alternatively, the stent may be coated with a Q attenuator to reduce vibrations to an efficacious level.

Figure 11:
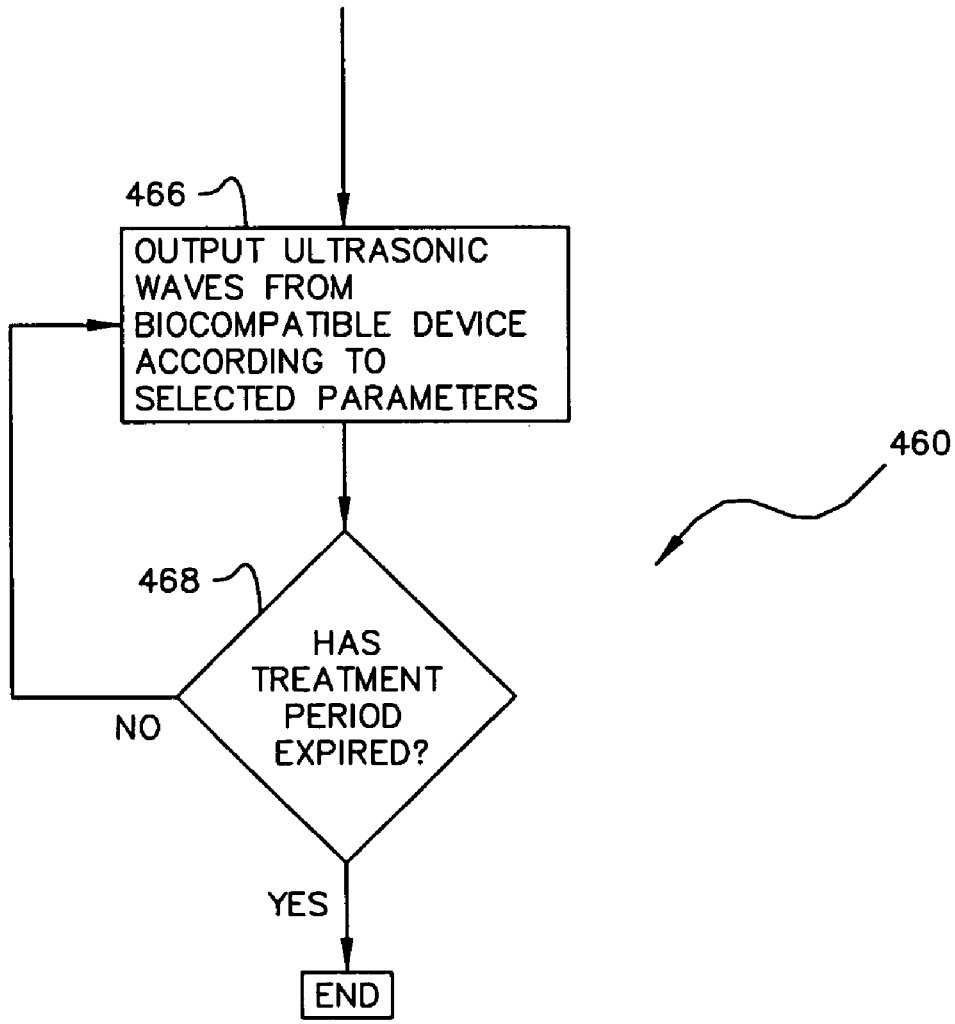
FIG. 11 shows an exemplary flow chart of the use of the present invention to provide treatment to a stent to prevent restenosis.

FIG. 11 shows an exemplary flow chart of a procedure 460 which uses the present invention to provide treatment to a stent 402 to prevent restenosis. In block 466, the ultrasonic emitter 138 is activated according to its controllable parameters, e.g., frequency and/or amplitude. At block 468, it is determined if the prescribed treatment period has been expired. If not, the process continues at block 466. Finally, in block 468, it is determined that there has been sufficient treatment has been provided and the process concludes in block 470. It is anticipated that these procedures will be repeated annually or bi-annually under medical supervision.

Additionally or alternatively it may be desired to controllably release a steroid eluting drug to prevent restenosis. Accordingly, the lattice portion that forms the biocompatible device 400 may be at least partially coated with a steroid eluting drug (see layer 500) that is controllably released in response to an electrical current, being passed between electrodes 112*a* (E1) and 112B (E2). Control of this current is done by the controller 106 in response to data received from external controller 406. Alternatively or additionally, at least a portion of the lattice that forms the stent 402 may be at least partially coated (see layer 502) with a steroid eluting drug and an electrical pathway (see pathway 504) may allow a current to flow though the selected portions of the stent 402 and thereby controllably release the steroid eluting drug.

Accordingly, what has been shown are systems and methods for preventing restenosis following a stent procedure by using an improved stent having at least one biocompatible device formed as an integral portion of its lattice structure where the at least one biocompatible device is under control of an externally-positioned control device that issues commands to the at least one biocompatible device to use an electrically controlled signal to cause the at least one biocompatible device to minimize plaque accumulation on the stent. While the application has been primarily directed toward stents implanted in blood vessels, e.g., coronary arteries, stents implanted in other body vessels, i.e., ducts, canals, or other tubes that contain or convey a body fluid are also considered to be within the scope of the present invention. For example, certain medical conditions require the prolonged use of a stent within the ureter of a patient. Periodically, these stents require replacement due to buildup, referred to as plaque in this application, on the stent. Accordingly, the present invention is useful with this class of stents as well. Thus, while the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A stent for preventing restenosis following placement in a vessel of a patient, said stent comprising:
    an expandable wire mesh tube comprised of a plurality of integral lattice portions and configured for expansion within the blood vessel of the patient;
    an electrically-powered biocompatible device proximate at least one of said integral lattice portions wherein said biocompatible device is comprised of:
        a controller within said biocompatible device responsive to an externally-provided command signal; and
        an ultrasonic emitter within said biocompatible device coupled to said controller for emitting an ultrasonic wave to induce mechanical vibrations in said wire mesh to thereby minimize forming plaque on said stent;
    said biocompatible device including a power receiving structure for producing a voltage to power said controller and said ultrasonic emitter in response to an externally-provided AC magnetic field.

2. A stent for preventing restenosis following placement in a vessel of a patient, said stent comprising:
    an expandable wire mesh tube comprised of a plurality of integral lattice portions and configured for expansion within the blood vessel of the patient;
    an electrically-powered biocompatible device proximate at least one of said integral lattice portions wherein said biocompatible device is comprised of:
        a controller within said biocompatible device responsive to an externally-provided command signal; and
        an ultrasonic emitter within said biocompatible device coupled to said controller for emitting an ultrasonic wave to induce mechanical vibrations in said wire mesh to thereby minimize forming plaque on said stent;
    said biocompatible device including a power receiving structure for producing a voltage to rower said controller and said ultrasonic emitter in response to an externally-provided AC magnetic field; and
    wherein said externally-provided AC magnetic field is amplitude modulated with said externally-provided command signal and said biocompatible device includes a receiving portion for responding to said command signal directed to said biocompatible device.

3. A stent for preventing restenosis following placement in a vessel of a patient, said stent comprising:
    an expandable wire mesh tube comprised of a plurality of integral lattice portions and configured for expansion within the blood vessel of the patient;
    an electrically-powered biocompatible device proximate at least one of said integral lattice portions wherein said biocompatible device is comprised of:
        a controller within said biocompatible device responsive to an externally-provided command signal;
        an ultrasonic emitter within said biocompatible device coupled to said controller for emitting an ultrasonic wave to induce mechanical vibrations in said wire mesh to thereby minimize forming plaque on said stent;
    said biocompatible device including a power receiving structure for producing a voltage to power said controller and said ultrasonic emitter in response to an externally-provided AC magnetic field;
    said externally-provided AC magnetic field amplitude modulated with said externally-provided command signal and said biocompatible device including a receiving portion for responding to said command signal directed to said biocompatible device; and
    wherein said command signal includes instructions to determine parameters of said ultrasonic wave selected from the set of the frequency and the amplitude of said ultrasonic wave.

* * * * *

UNITED STATES PATENT AND TRADEMARK OFFICE
CERTIFICATE OF CORRECTION

PATENT NO. : 7,563,279 B2
APPLICATION NO. : 11/157646
DATED : July 21, 2009
INVENTOR(S) : Brian J. Lasater It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (739) days Delete the phrase "by 739 days" and insert -- by 782 days --

Signed and Sealed this

Third Day of November, 2009

David J. Kappos
*Director of the United States Patent and Trademark Office*